United States Patent
Das et al.

(12) 
(10) Patent No.: US 6,656,148 B2
(45) Date of Patent: Dec. 2, 2003

(54) INFUSION PUMP WITH A SEALED DRIVE MECHANISM AND IMPROVED METHOD OF OCCLUSION DETECTION

(75) Inventors: Kusal K. Das, Wrightstown, PA (US); Ian Maxwell Shipway, Ardmore, PA (US)

(73) Assignee: Animas Corporation, Frazer, PA (US)

(*) Notice: Subject to any disclaimer, the term of this patent is extended or adjusted under 35 U.S.C. 154(b) by 0 days.

(21) Appl. No.: 10/140,633

(22) Filed: May 7, 2002

(65) Prior Publication Data

US 2002/0128594 A1 Sep. 12, 2002

Related U.S. Application Data

(62) Division of application No. 09/335,999, filed on Jun. 18, 1999, now Pat. No. 6,423,035.

(51) Int. Cl.⁷ .............................................. A61M 31/00
(52) U.S. Cl. ................... 604/67; 604/155; 128/DIG. 1; 128/DIG. 12
(58) Field of Search ............................. 604/65, 67, 118, 604/131, 151, 154, 155, 156, 93.01; 128/DIG. 1, DIG. 12; 318/254, 685, 696; 417/44.1, 44.2, 53, 63

(56) References Cited

U.S. PATENT DOCUMENTS

| | | | |
|---|---|---|---|
| 3,771,694 A | 11/1973 | Kaminski | |
| 3,985,133 A | 10/1976 | Jenkins et al. | |
| 4,529,401 A | 7/1985 | Leslie et al. | |
| 4,544,369 A | 10/1985 | Skakoon et al. | |
| 4,685,903 A | 8/1987 | Cable et al. | |
| 4,919,650 A | 4/1990 | Feingold et al. | |
| 4,978,335 A | 12/1990 | Arthur, III | |
| 5,176,502 A | 1/1993 | Sanderson et al. | |
| 5,254,096 A | 10/1993 | Rondelet et al. | |
| 5,505,709 A | 4/1996 | Funderburk et al. | |
| 5,647,853 A | 7/1997 | Feldmann et al. | |
| 5,681,285 A | 10/1997 | Ford et al. | |
| 5,741,227 A | 4/1998 | Sealfon | |
| 5,954,697 A | 9/1999 | Srisathapat et al. | |
| 6,241,704 B1 * | 6/2001 | Peterson et al. | 604/65 |
| 6,362,591 B1 * | 3/2002 | Moberg | 318/685 |

* cited by examiner

Primary Examiner—Manuel Mendez
Assistant Examiner—Mark K. Han
(74) Attorney, Agent, or Firm—Finnegan, Henderson, Farabow, Garrett & Dunner, L.L.P.

(57) ABSTRACT

A piston-type infusion pump is provided having an improved method of occlusion detection. The infusion pump includes processing circuitry for controlling the drive mechanism to infuse medication to a patient, including a sensor to track the position of the syringe plunger, thereby metering the amount of medication dispensed to the patient. The processing circuitry also includes a force sensor for providing signals indicative of the presence of occlusions along the infusion path. The operation of the drive mechanism causes delivery of medication to the patient. The infusion pump is constructed to be watertight.

21 Claims, 13 Drawing Sheets

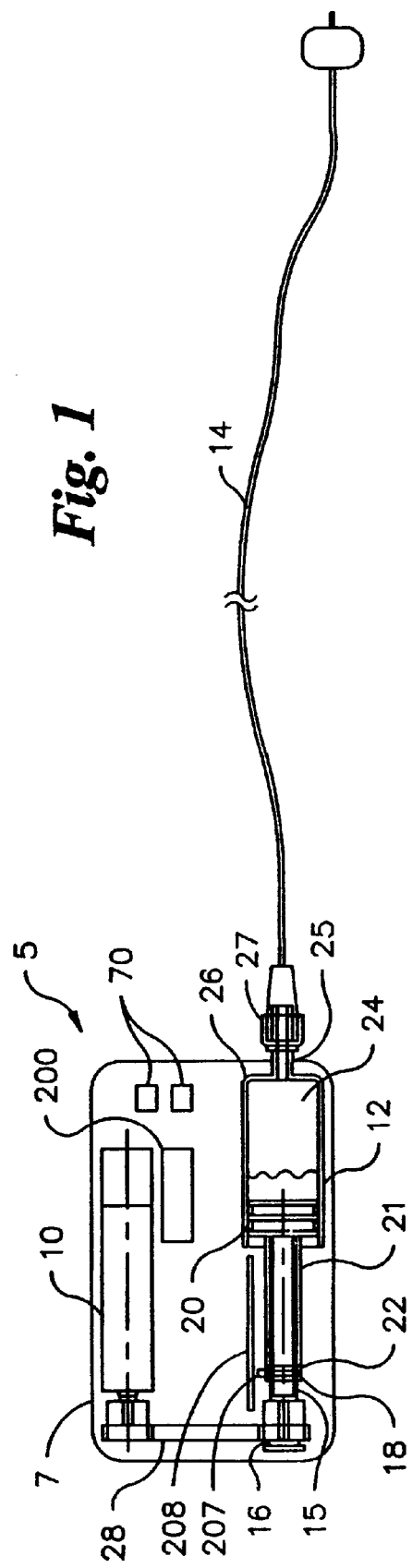

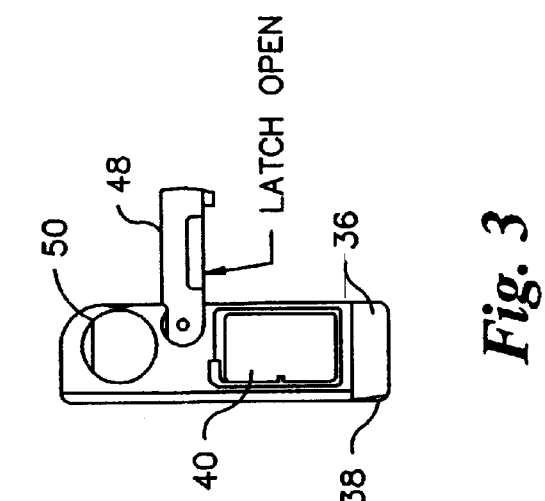
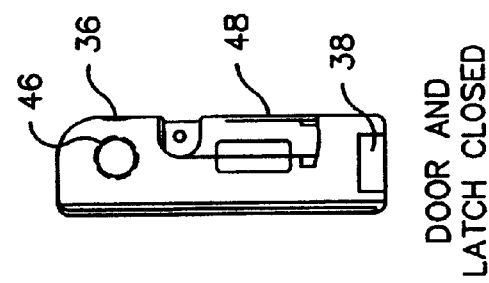
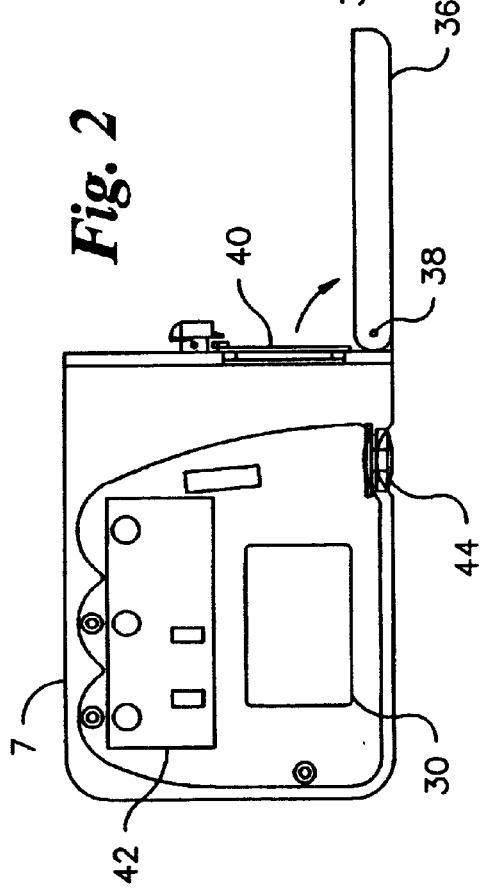
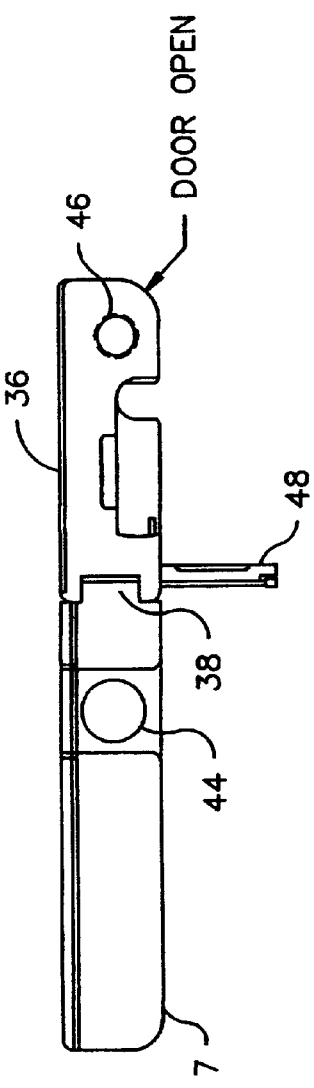

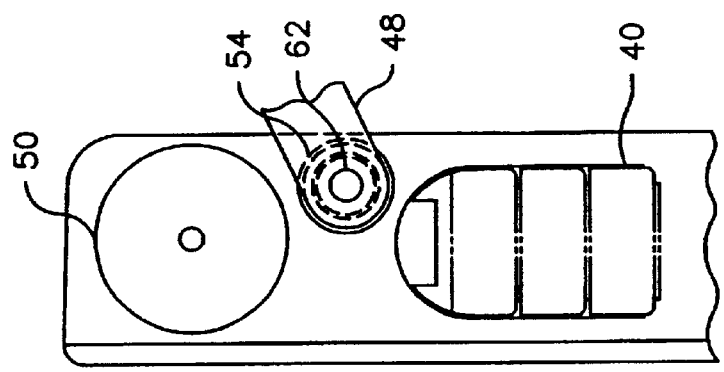
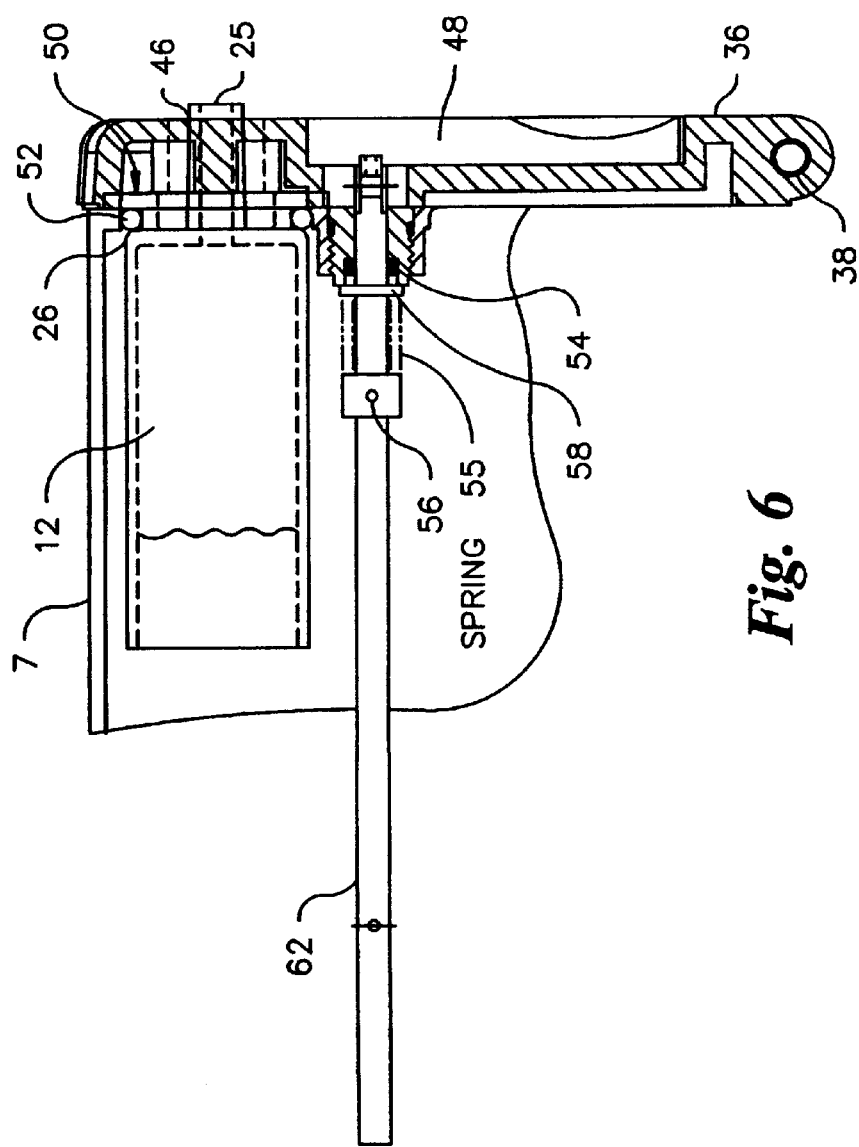

INFUSION PUMP WITH A SEALED DRIVE MECHANISM AND IMPROVED METHOD OF OCCLUSION DETECTION

CROSS-REFERENCE TO RELATED APPLICATIONS

This application is a division of copending U.S. application Ser. No. 09/335,999, filed Jun. 18, 1999 now U.S. Pat. No. 6,423,035 entitled: "Infusion Pump With A Sealed Drive Mechanism And Improved Method Of Occlusion Detection."

BACKGROUND OF THE INVENTION

The present invention relates to an infusion pump for controlled delivery of a pharmaceutical product to a subject, and more specifically to an infusion pump having a sealed drive mechanism and improved method of occlusion detection for determining the presence of obstructions in the infusion path.

Infusion pumps provide a significant lifestyle benefit for individuals requiring multiple deliveries of volumetrically proportioned medication to their body over a period of time. Infusion pumps reliably dispense the required medication to the patient through an infusion path established between the patient and the pump. The infusion path is a conduit secured to the pump at one end and secured intravenously or subcutaneously to a patient on the other. The operation of the infusion pump is controlled by a processor. The processor controls the delivery of periodic dosages of medication to a patient at predetermined times. Thus, a patient is able to rely on the infusion pump for delivering the required dosage of medication intravenously or subcutaneously over a period of time. In this way, the patient need not interrupt life activities for repeated manual delivery of required medication.

As is known, infusion pumps often employ a piston-type drive mechanism for urging the contents of a pharmaceutical cartridge or "syringe" internal to the pump along the infusion path to the subject. Piston-type infusion pumps are susceptible to an occlusion in the infusion path. Additionally, piston-type infusion pumps include complicated drive assemblies which require periodic maintenance and/or user adjustment which further degrades the reliability of the device.

Most piston-type infusion pumps have an exposed leadscrew drive assembly that is manipulated by the user to reset the device each time a new syringe is inserted in the device. Because the lead screw is a precision mechanical assembly that drives a plunger through the syringe to infuse pharmaceutical product along an infusion path, dirt and debris in the exposed lead screw can cause the screw thread to either wear-down or lock-up at its point of engagement with a mated drive, either of which can cause a pump failure. Some manufacturers suggest periodic cleaning of the lead screw, while the other manufacturers have equipped their devices with disposable lead screws and nut assemblies to prevent such malfunctions. Installation of these parts in some pumps requires partial disassembly of the device, further complicating syringe installation. Furthermore, many piston type infusion pumps are used with syringe plungers manufactured with "O"-rings. The installation of the syringe will often break the plunger seal about the O-ring and cause medication to leak through the plunger into the pump, possibly damaging electrical components, but also causing medication not being delivered properly to the patients through infusion set electronics. Moreover, there is a need for an infusion pump with sealed and inaccessible electronics so the pump does not become damaged due to accidental or deliberate submersion in water, and a sealed drive mechanism to prevent damage to the lead screw.

Often piston-type infusion pumps also do not show the amount of medication remaining in a syringe. Some manufacturers use a transparent window to visually inspect whether a syringe requires replacement. If a patient is not diligent about making such visual checks, he runs the risk of running out of medication. Other pumps indirectly determine the amount of remaining medication and, therefore, are subject to inaccuracies. Thus, there is a need for an infusion pump that directly reports the amount of remaining medication.

While some infusion pumps are designed to subtract delivery volumes from a fixed full or a fixed half syringe volume, the amount of medication in the syringe must be manually entered into the device at the outset by the patient upon installation of the syringe, although it may actually be neither full nor half full initially. This requirement is still a further complication of the syringe installation process.

Regarding occlusion detection, when an occlusion occurs anywhere along the infusion path of a piston-type pump, medication is not delivered to the patient even though the piston moves to deliver the medication. As can be appreciated, the existence of an occlusion will prevent the infusion pump from delivering medication to a patient until the occlusion is detected and cleared from the infusion path. Thus, the rapid detection of occlusions along the infusion path is key to reliable operation of a pump.

Presently, a piston-type infusion pump is desired which provides an improved method of occlusion detection, the pump including a simplified and reliable piston-type drive mechanism.

The present invention is directed to a piston-type infusion pump which includes an enclosed lead screw which can not be accessed without disassembling the pump. Thus, the engagement and disengagement of drive mechanism are achieved remotely, by latching and unlatching of the pump door, minimizing likely user error or abuse. The pharmaceutical syringe has a U-shaped plunger designed to link with the drive mechanism for simple installation. Additionally, the pump displays exact amount of medication (i.e., insulin) remaining in the cartridge at any time and utilizes an improved method of occlusion detection.

BRIEF SUMMARY OF THE INVENTION

Briefly stated, the present invention provides a piston-type infusion pump having a remotely engaged piston-type drive mechanism and improved method of occlusion detection. The internal components of the pump are sealed from the outside when a pharmaceutical syringe is installed, thus creating a watertight seal when the pump is in its operational mode.

The infusion pump is designed to remotely engage and disengage the lead screw of a drive mechanism by way of a latch stem, which is a part of a pump door latching mechanism. The pump door latch has a watertight rotary seal between the casing of the infusion pump and the latch stem. When the pump door latch is moved up to allow the pump door to open, it disengages the drive, so that the plunger of the syringe is free to move. When the pump door latch is pushed down to lock the pump door of the infusion pump, it engages the drive. When in the locked position the plunger is moved only through rotation of the lead screw. Thus, the engagement and disengagement of drive mechanism are achieved remotely, by latching and unlatching of the pump door, minimizing likely user error or abuse.

The infusion pump includes processing circuitry for controlling the drive mechanism to infuse medication to a patient, including a sensor to track the position of the syringe plunger. The sensor provides information that determines the volume of remaining insulin at any time in the pump. The infusion pump processing circuitry also includes a force sensor and circuitry for uniquely processing signals indicative of the presence of an occlusion along the infusion path. The occlusion detector operates with good accuracy at low volumes and delivery rates.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 1 is top view of the infusion pump with the top wall of the casing removed to show the layout of the components in accordance with a preferred embodiment of the present invention;

FIG. 2 is a top view of the infusion pump shown in FIG. 1 with the pump door open;

FIG. 3 is a front view of the pump door and latch assembly of the infusion pump shown in FIG. 1 with the latch in the open position and the pump door open for loading a syringe;

FIG. 4 is a front view of the infusion pump with the latch in the closed position and the pump door closed with the pump housing a syringe;

FIG. 5 is a side view of the infusion pump with the pump door open;

FIG. 6 is a side view of the latch stem assembly with the latch in the closed position and the pump door closed, with watertight seals in accordance with a preferred embodiment of the invention;

FIG. 7 is a front view of the latch stem assembly with the latch in the open position and the pump door open;

DETAILED DESCRIPTION OF THE INVENTION

Figure 9:
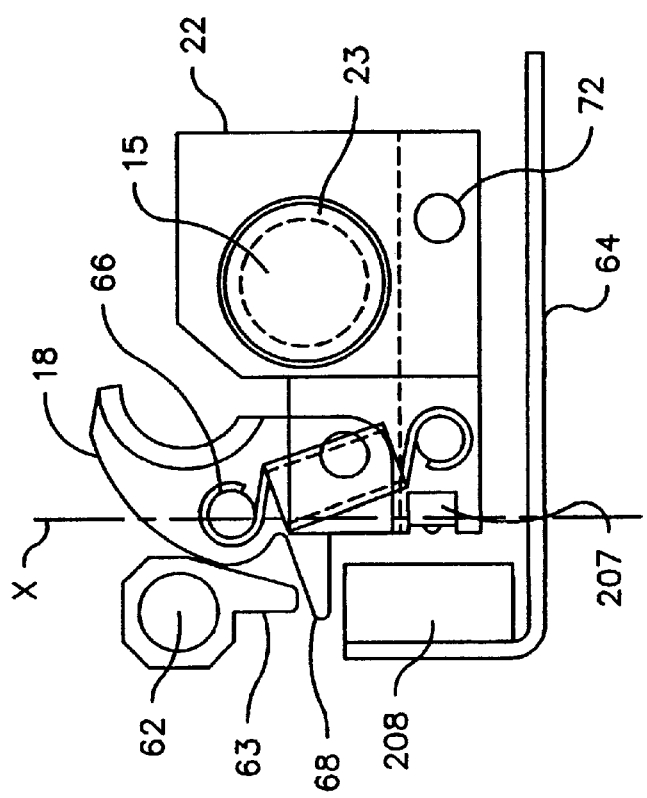
FIG. 9 is a front view of the lead screw and slide assembly in the disengaged position in accordance with the preferred embodiment of FIG. 6.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the infusion pump and designated parts thereof. The terminology includes the words specifically mentioned above, derivatives thereof and words of similar import.

The term "Bolus" as used herein refers to a dosage of medication which is large with respect to typical dosage levels. For example, when infusing insulin to a patient over a period of time, a bolus is typically delivered to a patient before or during a meal to compensate for the increased amount of insulin required to balance glucose produced by food, or when the blood glucose is high. "Basal" as used herein refers to the essential dosage of medication which must be delivered to a patient repeatedly over a period of time to maintain normal biological function.

Referring to FIG. 1, a piston-type infusion pump 5 in accordance with the present invention is shown for delivering medication 24 to a patient along an infusion path 14. The infusion pump 5 includes a sealed pump casing 7, processing circuitry 200, power cells 70, force sensor 16, LED 207, optical linear sensor 208, motor 10, lead screw 15, half nut 18, slide 22, syringe 12, gear train 28, and infusion path 14.

In operation, processing circuitry 200, powered by power cells 70, controls the operation of the infusion pump 5. The motor 10 is incrementally engaged to infuse medication to a patient at predetermined intervals. Upon engagement, the motor 10 causes the lead screw 15 to rotate by means of the gear train 28. When the half nut 18 is engaged with the lead screw 15 and the lead screw 15 is driven by the motor 10, the slide 22 traverses the slide rail 72 (see FIGS. 8–9) pushing the plunger 20 of the syringe 12. This causes delivery of medication 24 at the distal end 26 of the syringe 12. An infusion path 14 to deliver the medication 24 is connected by the connector 27 to the dispensing tip 25 of the syringe 12 to provide fluidic communication between the infusion pump 5 and a patient.

Referring now to FIGS. 2–5, the casing of the infusion pump 5 is shown. The pump casing 7 is preferably formed of a thermoplastic material and preferably made watertight by sealing any openings in the pump casing 7. The watertight pump casing 7 of FIGS. 2–5 preferably prevents damage to any components contained inside it. The pump casing 7 supports LCD display 30, keypad 42, priming button 44, battery door 40, exterior infusion port 46, hinge 38, pump door latch 48, and pump door 36.

LCD display 30 is a menu driven graphic display. In this embodiment the display items are listed vertically allowing the patient to scroll through menus until finding the desired item to access status data or to program the infusion pump 5. Other display configurations of the LCD display 30 are possible in other embodiments, as well as the ability to display other information on the LCD display 30.

Figure 10:
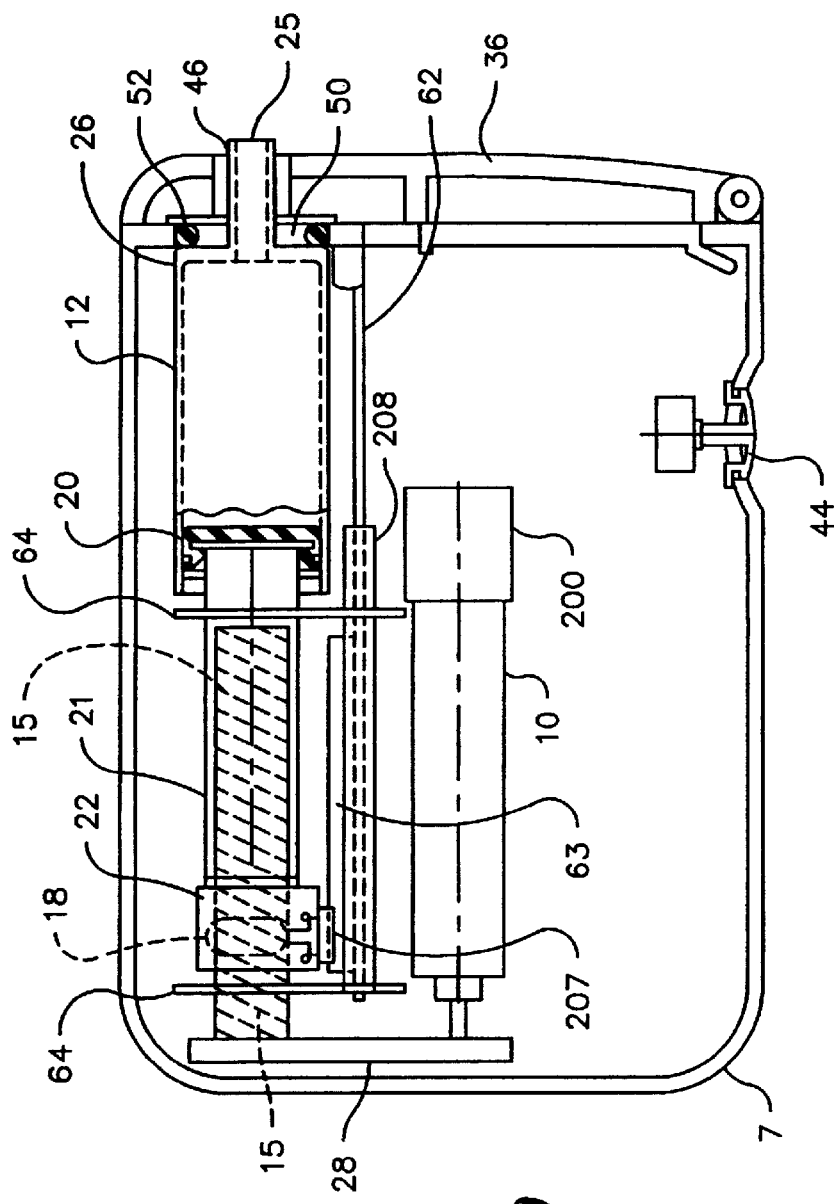
FIG. 10 is a top view of the lead screw and slide assembly engaging a syringe in the infusion pump in accordance with the preferred embodiment of FIG. 6.

FIGS. 2–5 show the syringe loading process. In FIGS. 2 and 3, the pump door 36 is opened to expose the interior infusion port 50 and the battery door 40. The syringe 12 is installed through interior infusion port 50, interior to the pump casing 7 of the infusion pump 5, creating a watertight seal. In FIGS. 2 and 3, the pump door latch 48 has been rotated away from the pump casing 7 in order to release the pump door 36 so it may pivot open at hinge 38. The release of pump door 36 enables the patient to rotate the pump door 36 about the hinge 38 thereby exposing interior infusion port 50 as shown in FIG. 3. Interior infusion port 50 is provided to receive a syringe 12 containing a supply of pharmaceutical product to be infused along the infusion path 14 by the infusion pump 5 as best shown in FIG. 10. The battery door 40 is removed for replacing the power cells 70. The battery door 40 preferably snaps into place and preferably includes a seal to maintain the watertight properties of the pump casing 7.

The syringe 12 ideally includes a plunger 20 and a plunger stem 21 for engagement with the slide 22 upon installation in the interior infusion port 50 (see FIG. 1). The syringe 12 is installed in the infusion pump 5 by rotating the pump door latch 48 away from the pump door 36 of the infusion pump 5 as shown in FIGS. 3 and 5. The pump door 36 is then rotated away from the infusion pump 5 about the hinge 38, exposing the interior infusion port 50, which receives the syringe 12. The pump door 36 closes in the opposite manner of opening, and the pump door latch 48 is rotated back into place, locking the pump door 36 as shown in FIG. 4.

Referring now to the preferred embodiment of FIGS. 6 and 7, there is preferably an elastomeric O-ring 52 assembled on the inside diameter of interior infusion port 50. The O-ring 52 provides a seal between the pump casing 7 and the syringe 12. When the syringe 12 is installed in the interior infusion port 50 of the pump casing 7, the pump door 36 is closed and latched in place by rotating the pump door latch 48 over the pump door 36. As pump door 36 is closed, the syringe 12 is pushed against the pump casing 7 as shown in FIG. 6, and the O-ring 52 is squeezed in the interior infusion port 50 creating a seal at the distal end 26 of the syringe 12. The interior infusion port 50 is preferably the only opening in the pump casing 7. Thus the inside of the pump casing 7 is preferably sealed from outside contaminants, creating a watertight seal.

Pump door latch 48 is fixedly mounted on latch stem 62 which extends along the interior length of the interior of pump casing 7. The axis of latch stem 62 is parallel with the longitudinal axes of syringe 12 and lead screw 15. The latch stem 62 is held in the wall of pump casing 7 by a rotary seal 54. Seal 54 is held in place by bias spring 55 and washer 58, which are held in place over latch stem 62 by collar 56. Upon rotation of pump door latch 48 to secure the syringe 12 within interior infusion port 50, the translation of the pump door latch 48 to the closed position causes a rotation of the latch stem 62. Rotation of latch stem 62 moves the half nut 18 into engagement with the lead screw 15 as shown in FIGS. 8 and 9.

Figure 8:
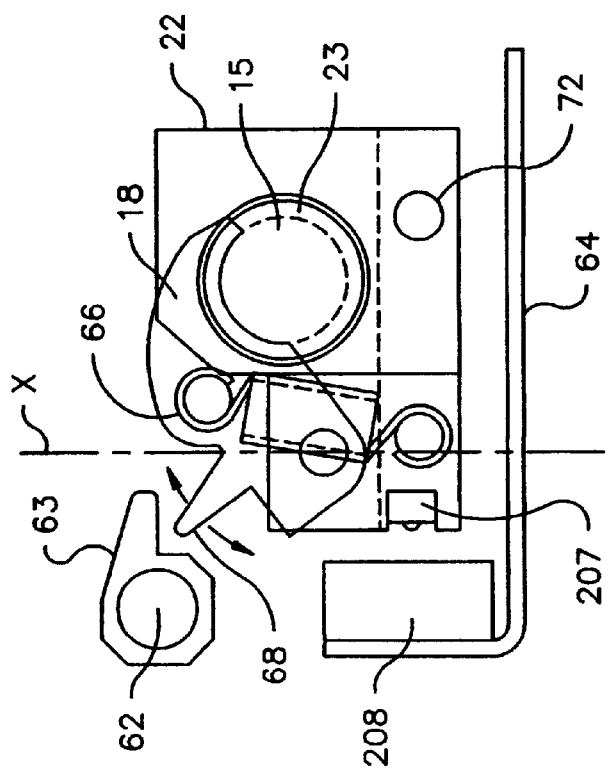
FIG. 8 is a front view of the lead screw and slide assembly in the engaged position in accordance with the preferred embodiment of FIG. 6.

FIGS. 8 and 9 show the mechanism for the preferred embodiment of FIG. 6 that engages and disengages the half nut 18 to the lead screw 15 through rotation of the pump door latch 48 and latch stem 62. The lead screw 15 is mounted on a carriage 64 (the carriage 64 mounted to the pump casing 7) so as to be parallel with latch stem 62. The half nut 18 is attached to the slide 22. In FIG. 8, when the pump door latch 48 is moved to lock the pump door 36, it also rotates latch stem 62 to disengage cam 63 from nut lever 68, and moves the half nut 18 to engage the lead screw 15. The spring 66 is anchored to the half nut 18 and to the slide 22 as shown. Spring 66 holds the half nut 18 to the right side of the axis X when the cam 63 releases the nut lever 68, thereby holding the half nut 18 in the engaged position.

Likewise, in FIG. 9, when the pump door latch 48 is rotated away from the pump door 36 to unlock the pump door 36, it also turns the latch stem 62. Cam 63 consequently pushes down on the nut lever 68 and, hence moves the half nut 18, to the disengaged position, where it is held on the left side of the axis X by the spring 66. This releases the slide 22 to move to any position along the slide rail 72 when pushed by the plunger stem 21 of syringe 12. The lead screw 15, latch stem 62, the slide 22 and the half nut 18 are all preferably sealed internal components to the pump 5 and are not accessed by the user.

A buttress thread is preferably used for the lead screw 15 and the half nut 18, since the lead screw 15 engages and pushes the half nut 18 only in one direction. The wear components e.g., the lead screw 15 and the half nut 18 are preferably coated with a low friction, wear resistant coating to prolong life and to reduce power required to drive the infusion pump 5.

FIGS. 8 and 9 also show how the amount of medication 24 remaining in the syringe 12 can be determined by the processing circuitry 200 at any given time. A light source, LED 207 is mounted on the slide 22. An optical linear sensor 208 is fixedly mounted to the carriage 64. The position of the slide 22 can be accurately measured at any moment by the optical linear sensor 208 by determining location of the LED 207 relative to the sensor 208. The position of the slide 22 also determines the position of the plunger 20. Since the diameter and position of the syringe 12 are known, based on the position of the slide 22, the amount of medication 24 remaining in the syringe 12 can also be determined by the processing circuitry 200 as described herein.

Figure 11:
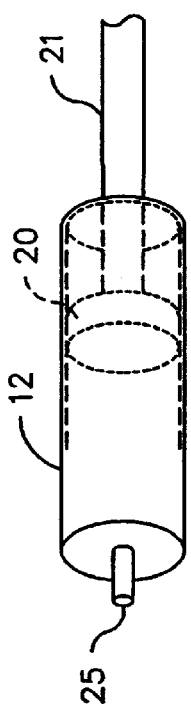
FIG. 11 is a side perspective view of the syringe and plunger assembly.

Referring now to FIG. 11, a syringe 12 for use with the infusion pump 5 is shown. The syringe 12 includes a plunger 20 which preferably includes a generally elongated, "cup-shaped" plunger stem 21 and a dispensing tip 25. In FIG. 10 the plunger stem 21 contacts the slide 22 so that the slide 22 may push the plunger stem 21 when engaged by the half nut 18 and urged by the lead screw 15. The plunger stem 21 is preferably cup-shaped so that the lead screw 15 may reside within the cavity created by the plunger stem 21, without exerting any pressure on the plunger 20 or the plunger stem 21. The slide 22 includes an aperture 23 (see FIGS. 8 and 9), larger than the diameter of the lead screw 15, such that the lead screw 15 passes through the slide 22 to engage the half nut 18 and the gear train 28. Upon installation of the syringe 12 in the interior infusion port 50 of the pump casing 7, the plunger 20 normally advances the slide 22 axially away from the exterior infusion port 46 along the slide rail 72. The slide 22 is free to move, because, when the pump door 36 is open, the half nut 18 is rotated out of engagement with the lead screw 15.

In operation, the patient primes the infusion pump 5 to remove air from the infusion path 14 by depressing the priming button 44 until the infusion path 14 is free from air bubbles. In priming mode, the motor 10 drives medication 24 along the infusion path 14 until the patient is satisfied that the infusion path 14 is clear of air. Once the infusion pump 5 is primed the device is ready for programmed operation for a basal rate or bolus operation depending on the patient's requirements.

In programmed operation, the motor 10 causes the lead screw 15 to rotate by means of the gear train 28. When the half nut 18 engages the lead screw 15 and the lead screw 15 is driven by the motor 10, the rotation of the lead screw 15 moves the half nut 18 and the slide 22 traverses the slide rail 72 pushing the plunger 20 of the syringe 12. This causes delivery of medication 24 at the distal end 26 of the syringe 12. An infusion path 14 is linked to exterior infusion port 46 to deliver the medication 24 to a patient.

Processing Circuitry

Figure 12A:
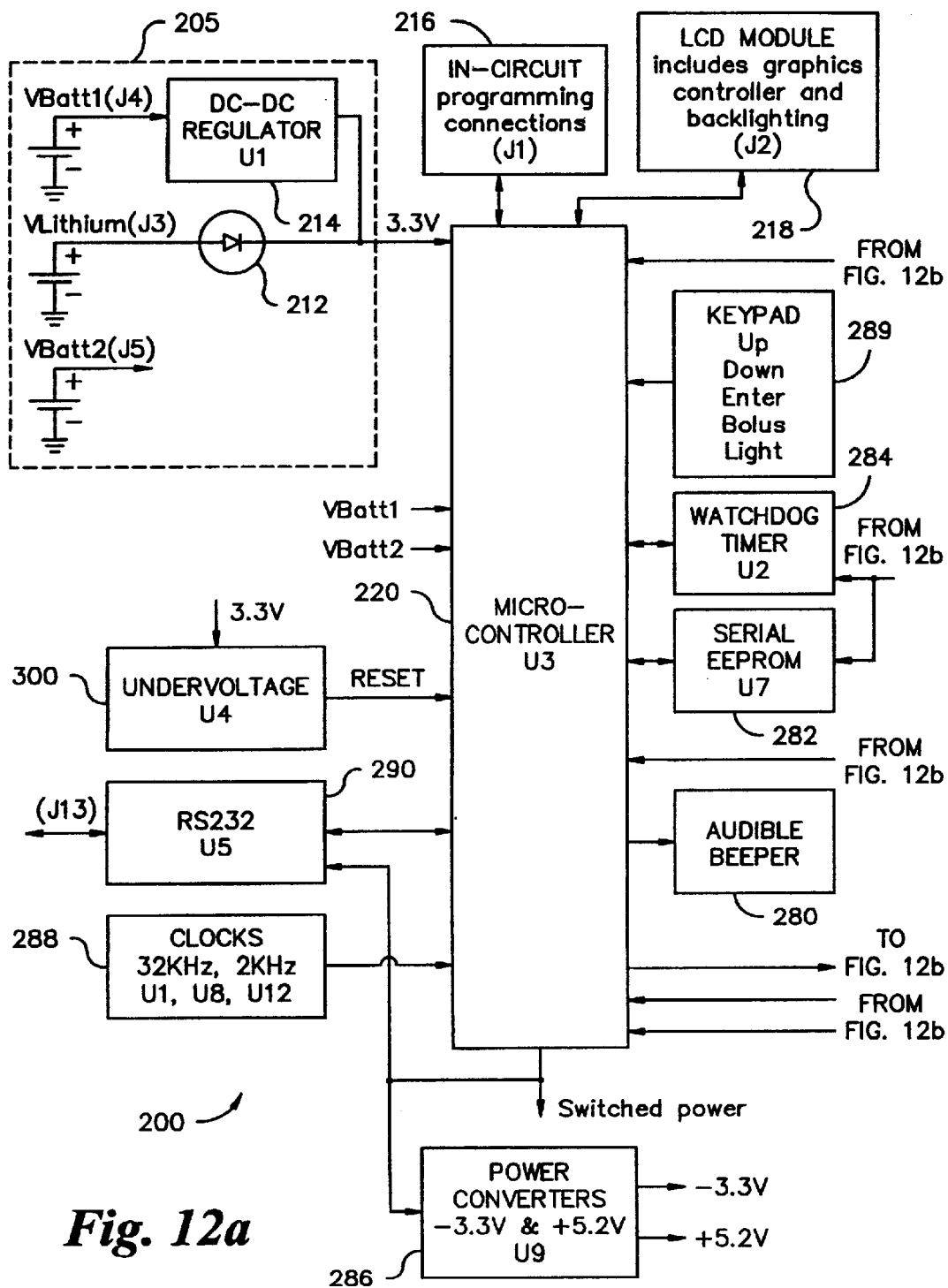
FIGS. 12a and 12b are block diagrams of the circuitry of the infusion pump in accordance with the preferred embodiment of FIG. 10.
Figure 12B:
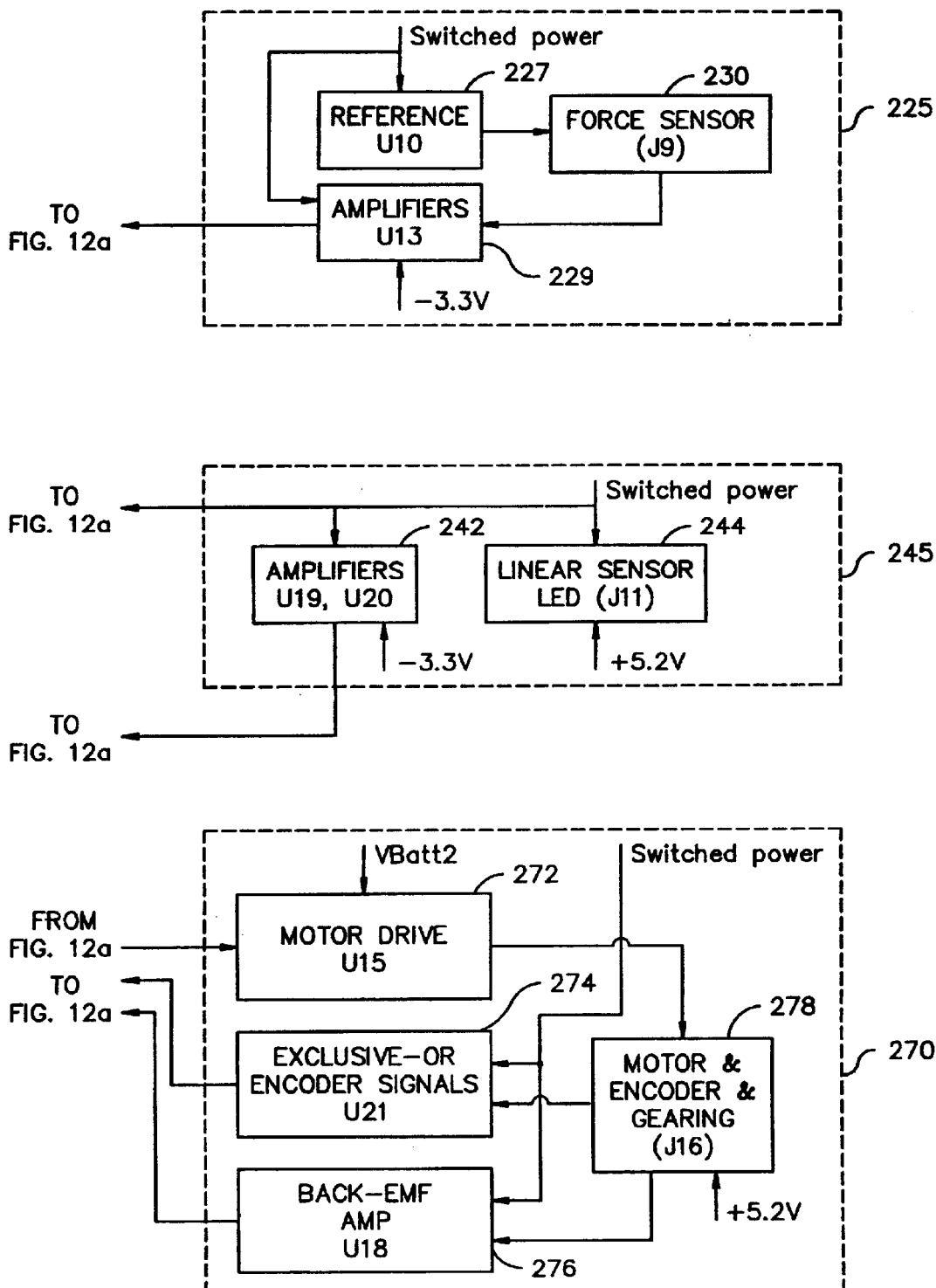

Referring now to FIGS. 12a and 12b, a block diagram of processing circuitry 200 of the preferred embodiment of the infusion pump 5 is shown. Processing circuitry 200 includes: processor 220, power section 205, force sensor section 225, position sensor section 245, motor drive section 270, as well as additional interface and signal conditioning circuitry described hereinafter.

Power section 205 preferably includes three sources of power for the infusion pump 5, although other embodiments may utilize different power configurations. In the preferred embodiment of FIGS. 12a and 12b Vbatt1 and Vbatt2 (power cells 70 in FIG. 1) are each preferably 2 silver oxide batteries in series. Vlithium is a backup source when Vbatt1 and Vbatt2 are low or are being replaced. Power section 205 is connected to the processing circuitry 200 by diode 212. Vlithium provides enough power to keep the system clock circuit 288 running. Vbatt1 provides power to the 3.3 Volt DC-DC regulator 214. The regulator 214 provides 3.3V to the processing circuitry 200 with the exception of the LCD module 218. Vbatt2 provides power to the motor drive 272 and the LCD module 218. The processor 220 switches the 3.3V power to the various sub-systems as they require power.

In an alternative embodiment, Vlithium is not used, and instead the 32 KHz clock 288 is replaced by a lower power real time clock (RTC) circuit. The RTC is powered by the 3.3V regulator through a diode. When the batteries are low or they are being replaced the RTC will be powered from a charge stored in a capacitor.

A power converter 286 provides −3.3V and +5.2V as needed by various subsystems.

Processor and Support Circuits

The processor 220 is a microprocessor or microcontroller integrated with memory and peripherals. The processor 220 preferably operates at 8 MHz. This is supplied from a quartz crystal (not shown). The processor 220 monitors the force sensor section 225 and the position sensor section 245 and controls the motor drive section 270 in accordance with an instruction set as described below. The processor 220 also determines the battery voltages and will alarm the user when it is time to replace the batteries through the audible beeper 280 and/or LCD module 218. A 32 KHz signal is also generated by system clock circuit 288 which is used when the processor 220 is placed in sleep mode. If the circuit power (3.3V from the regulator 214) drops below a threshold, the processor 220 will be placed in reset by under voltage circuit 300.

Serial communications circuit 290 is an RS-232 port. The serial communications circuit 290 is provided for test purposes.

Keypad circuit 289 is an interface which allows the user, through keypad 42, to program the infusion pump 5, view status and history, deliver a bolus and turn on a back light for the LCD display 30.

The LCD module 218 consists of LCD display 30 and graphics controller/driver and backlighting. The graphics controller/driver integrated circuit is controlled through a parallel interface (not shown) from the processor 220. A 2 KHz clock signal is provided to the LCD module 218 by system clock circuit 288; Vbatt2 provides the power to LCD module 218.

A watchdog timer 284 is used to ensure that the pump motor 10 is stopped if the instruction set of processor 220 has lost control of the infusion pump 5 or if a diagnostic test fails.

The non-volatile memory 282 is preferably an EEPROM used to store user programmable variables and pump history data for use by the instruction set of processor 220.

Force Sensor Section

Force sensor section 225 includes FSR circuit 230 (including force sensor 16), reference voltage circuit 227, and amplifier circuit 229.

A DC motor 10 of the infusion pump 5 drives the lead screw 15 that drives the plunger 20 of syringe 12 to deliver medication 24 to a patient along the infusion path 14. An FSR (force sensitive resistor) circuit 230, through force sensor 16, is used to sense the force on the lead screw 15 prior to the initiation of the delivery cycle. If there is an occlusion (an obstruction in the infusion path 14) the force on force sensor 16 will increase and will be detected by the processor 220. Similarly, if there is a leakage or absence of the syringe 12 within the infusion pump 5, the force sensor 16 will reflect a low force value. The processor 220 will alarm the user through audible beeper 280 and/or LCD module 218.

A 2.5V reference is supplied to the FSR circuit 230 and the output is amplified by amplifier circuit 229 before it is digitized by the processor 220. The processor 220 monitors the force and applies an algorithm (as described herein) to detect if an occlusion has occurred.

Position Sensor

Position Sensor Section 245 includes linear sensor circuit 244, and amplifier circuit 242.

An optical linear sensor 208 of linear sensor circuit 244, such as a linear sensor manufactured by Hamamatsu Corp., is used to track the motion of the plunger 20. The main function of the optical linear sensor 208 is to provide information that determines the volume of medication 24 remaining in the infusion pump 5 at any time. The linear sensor signal is also used to monitor any gross inaccuracy in medication 24 delivery by calculating delivery volume between any two points of time.

The optical linear sensor 208 is attached to the infusion pump 5 in a known, fixed position. The LED 207 of linear sensor circuit 244 is attached to the slide 22 that is moved to push the plunger 20 to cause delivery of medication 24. By knowing the position of the LED 207, the processor 220 calculates the position of the plunger 20. Since the syringe 12 is of a known diameter and is in a fixed position in the infusion pump 5, the position of the plunger 20 is used to determine the volume of remaining medication 24 in the syringe 12 at any time.

The optical linear sensor 208 of linear sensor circuit 244 is preferably a two electrode photo-diode device that provides continuous position data of light spots traveling over its surface. The current at each electrode of the optical linear sensor 208 is inversely proportional to the distance of the light source from the electrode. When the LED 207 is pulsed on, the current from each electrode of the optical linear sensor 208 is inversely proportional to the distance of the LED 207; by using two electrodes, errors due to power fluctuations can be minimized. The electronic pulses on the LED 207 cause current to flow from each of the sensor's electrodes. The currents are fed into trans-impedance amplifiers 242 and the processor 220 reads and digitizes the amplified current and applies an algorithm to determine and monitor the position of the plunger 20.

For example, in the preferred embodiment, the algorithm used to determine the medication 24 remaining (based on 300 units in a full syringe of U100 concentration insulin):

Units=$G1[A-B]/[A+B]+[150-K1]$ $G1=[37/25.5778]*150$

A=8 bit digitized value of sensor A output
B=8 bit digitized value of sensor B output
K1=offset value from calibration routine or=$G1[A$center-of-travel$-B$center-of-travel$]/[A$center-of-travel$+B$center-of-travel$]$ Motor Drive Motor drive section 270 includes motor circuit 278, encoder circuit 274, and amplifier circuit 276.

The output of an integrated DC motor 10 of motor circuit 278, encoder and gear reducers are used to drive the lead screw 15 that moves the plunger 20 of the infusion pump 5. The motor 10 is driven by a PWM (pulse width modulated) signal which is provided by the processor 220.

The motor 10 of motor circuit 278 is a closed loop velocity control with the feedback signal being the back-EMF of the motor which is amplified by the amplifier circuit 276. The closed loop control algorithm is a proportional type of control. The motor 10 is commanded to a constant speed and the processor 220 counts the pulses from the encoder circuit 274. When the motor 10 has moved the required number of pulses, the PWM signal from the processor 220 is turned off and a brake is applied. On the next maneuver the processor 220 will compensate for any undershoot or overshoot of the previous maneuver. For a basal delivery the motor 10 will move the lead screw 15 every 3 minutes. For the minimum required basal rate of 0.1 units/hr (1 microliter/hr) this means 0.005 units or 0.05 microliters is delivered every 3 minutes.

Figure 13:
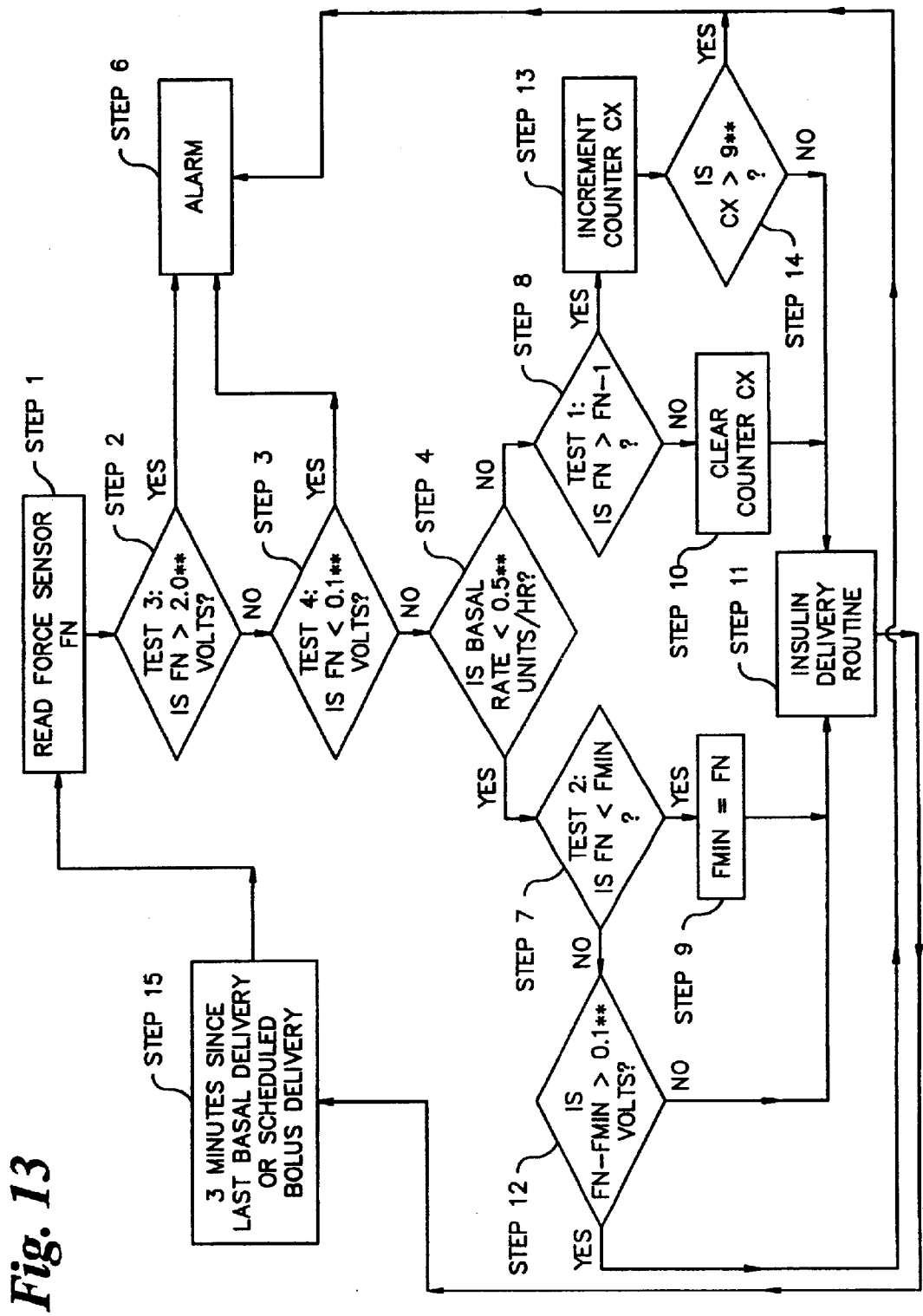
FIG. 13 is a flow chart of a preferred system failure detection method employed by the circuitry of FIGS. 12a and 12b.

Referring now to FIG. 13 (and the respective step numbers), a method of detecting an occlusion or leakage in the infusion path 14 of the infusion pump 5 is shown. FIGS. 15–19 show the individual methods of occlusion and leakage detection which the infusion pump 5 utilizes. When an occlusion or leakage occurs anywhere in the infusion path 14, medication 24 is not properly delivered to the patient. The extra volume of medication not delivered to the patient must occupy space within the infusion path 14 or the syringe 12. The infusion path 14 and syringe 12 are preferably made of semi-rigid or semi-flexible plastic. An increase in medication volume causes an increase in pressure within the medication fluid which can be monitored as force incident on the force sensor 16 at the end of the lead screw 15. As such, where medication 24 is frequently delivered (e.g., basal delivery every 3 minutes), this pressure increases with each delivery if the infusion path 14 is and remains occluded. Thus, the force sensor 16 located at the end of the lead screw 15 will encounter increased force prior to every delivery cycle of medication if there is an occlusion present in the infusion path 14.

At the outset of a delivery cycle, step 1 in FIG. 13, the processor 220 reads the signal of the force sensor circuit 230 which indicates the amount of force (FN) incident to the force sensor 16. The signal FN is passed to the processor 220 and is then compared to a reference value in step 2, FMAX, in this example, 2 volts. This process (see FIG. 15) will detect an occlusion in the system, since in all cases the FN reading should be less than the reference value. The reference value FMAX is stored in the non-volatile memory 282 of the processing circuitry 200. If the signal FN is greater than this value, an occlusion is present and the audible beeper 280 is sounded in step 6. Otherwise the process moves to step 3.

In step 3 of FIG. 13 (see also FIG. 16), the force signal FN is compared to a minimum threshold reference value to determine whether or not a syringe 12 having medication 24 is properly loaded in the infusion pump 5. This minimum reference value, FLEAK, is also stored in the memory 282 of the processing circuitry 200. If the signal FN at the force sensor 16 does not exceed the minimum threshold, the alarm is sounded in step 6. Such a condition also indicates possible leakage in the infusion pump 5 or in the infusion path 14 or the absence altogether of a syringe 12 in the infusion pump 5.

For the lowest basal rate the force signal FN does not always increase under occlusion conditions. This is because, at such a low basal rate, the increase in force due to occlusion is sometimes less than the variation in the force signal FN due to the drive mechanism turning the lead screw 15. Thus, a particular method is required to detect an occlusion if an extremely low basal rate is being used. In step 4 of FIG. 13 (see also FIG. 17), the processor 220 determines the present basal rate. If the rate is less than the predetermined threshold, BMIN, the process proceeds to step 7.

As shown in step 7 of FIG. 13, for a low basal rate, the force signal value FN is compared to a stored minimum value, FMIN. If the force signal FN is greater than FMIN the process proceeds to step 12. In step 12 the amount by which FN exceeds FMIN is determined. If the amount that FN exceeds FMIN (FN−FMIN) is greater than a predetermined threshold, FINC (here 0.1 volts), an occlusion has been detected, and the process proceeds to step 6 to sound the audible beeper 280; if FN does not exceed FMIN by the predetermined threshold FINC (i.e., FN−FMIN is less than 0.01), the process proceeds to step 11 and delivers medicine 24 along the infusion path 14 by incrementally moving the plunger 20.

In step 7 of FIG. 13, if FN is less than a stored minimum value FMIN, step 9 stores the current value of FN as the new FMIN in the memory 282 and the process proceeds to step 11 to delivers medication 24 along the infusion path 14 by incrementally moving the plunger 20.

Figure 18:
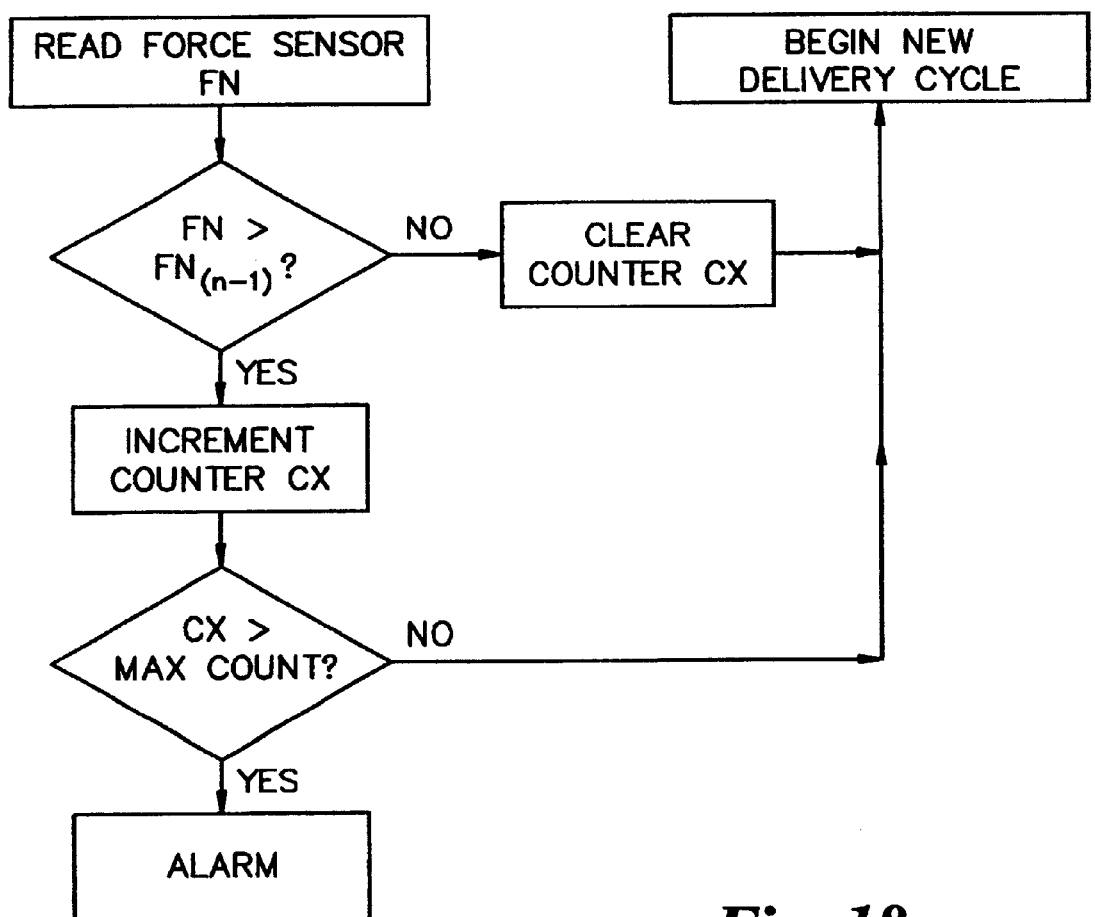

If step 4 determines that the basal rate is greater than a predetermined rate, the process proceeds to step 8 (see also FIG. 18). In step 8, FN is compared to the force signal from the previous delivery cycle, FN(n−1), stored in the memory 282. If in step 8 FN is greater than FN(n−1), a counter is incremented in step 13 to record an instance of increasing pressure from FN(n−1) to FN. If in step 14 the counter shows increasing pressure for a predetermined number (greater than 1) of cycles, an occlusion is declared and the beeper 280 is sounded in step 6. Otherwise the process proceeds to step 11 and delivers medication 24 along the infusion path 14 by incrementally moving the plunger 20.

If the signal FN in step 8 does not exceed FN(n−1), the counter is reset to zero in step 10 and the process proceeds to step 11 to deliver medication 24 along the infusion path 14 by incrementally moving the plunger 20.

Figure 19:
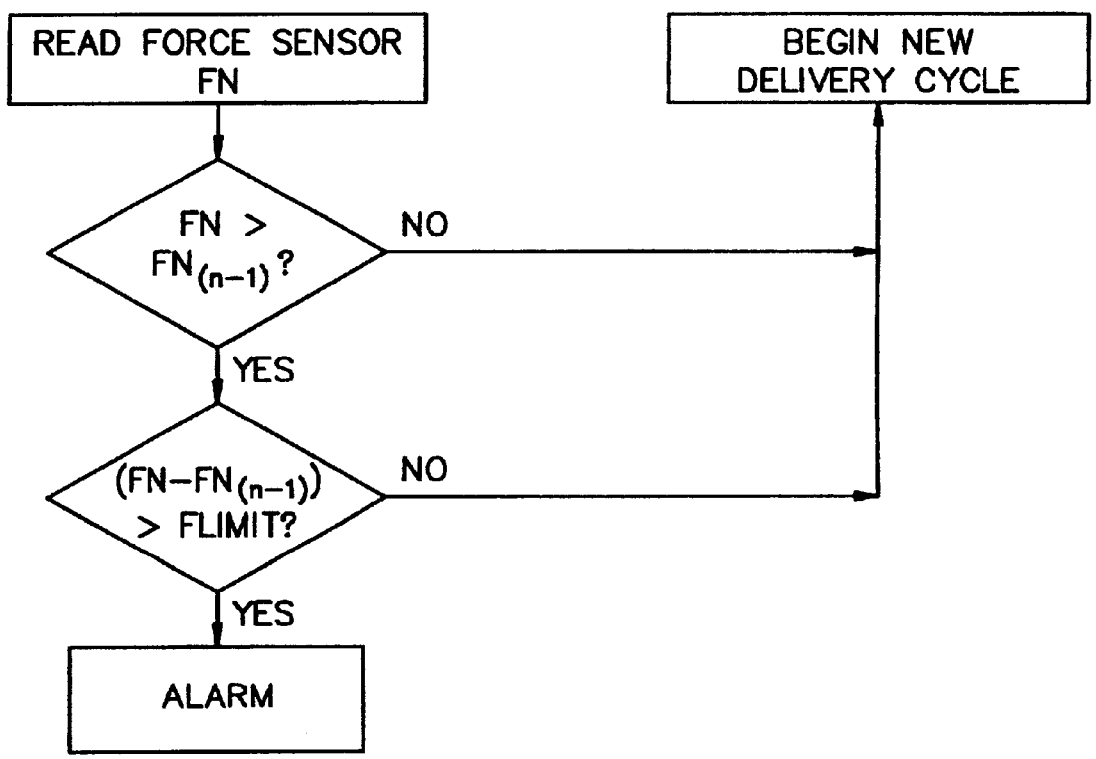

FIG. 19 reflects an occlusion detection method whereby step 8 compares FN to the force signal from the previous delivery cycle, FN(n−1). If the FN is greater than FN(n−1) by a predetermined maximum amount, FLIMIT, the beeper is sounded in step 6 without incrementing or checking the counter in step 13. If FN is not greater than FN(n−1) by FLIMIT, the counter is reset to zero in step 10 and the process proceeds to step 11.

Prior to initiating the delivery cycle over again, the processor proceeds to step 15 to wait until a predetermined time has passed.

Thus, the infusion pump 5 determines the presence of an occlusion in the infusion path 14 by processing force measurements from the force sensor 16 if one of the following occurs:

If the force measured during a delivery cycle, at a point immediately before the start of the subsequent delivery of medication, is greater than the force at the identical point in the previous cycle, and has been so for a predetermined number of delivery cycles, i.e.:

$F1<F2<F3<F4, \ldots FN(n-1)<FN$ for a predetermined number of cycles.

If the force measured during a delivery cycle, at a point immediately before the start of the subsequent delivery of medication, is greater than the force at the identical point in the previous cycle by an amount greater than a predetermined value, i.e.:

$FN-FN(n-1)>FLIMIT$.

If, in situations using low basal rates, the difference in force value taken during a cycle, at a point immediately before the start of the subsequent delivery of medication, and the force value at an identical point from any previous cycle for low basal rates, is greater than a predetermined value, i.e.:

$(FN-FMIN)>$a predetermined value, $FINC$.

If the force measured during a cycle, at a point immediately before the start of the subsequent delivery of medication is greater than a predetermined value, i.e.:

$FN>$a predetermined value, $FMAX$.

The force measurements are also used to detect if the syringe 12 is removed, or if the infusion path 14 is not connected to exterior infusion port 46. In these cases the force measured will be close to zero and the infusion pump 5 will alarm the user to check the syringe 12 and infusion path 14 for possible leakage or other condition.

Figure 14:
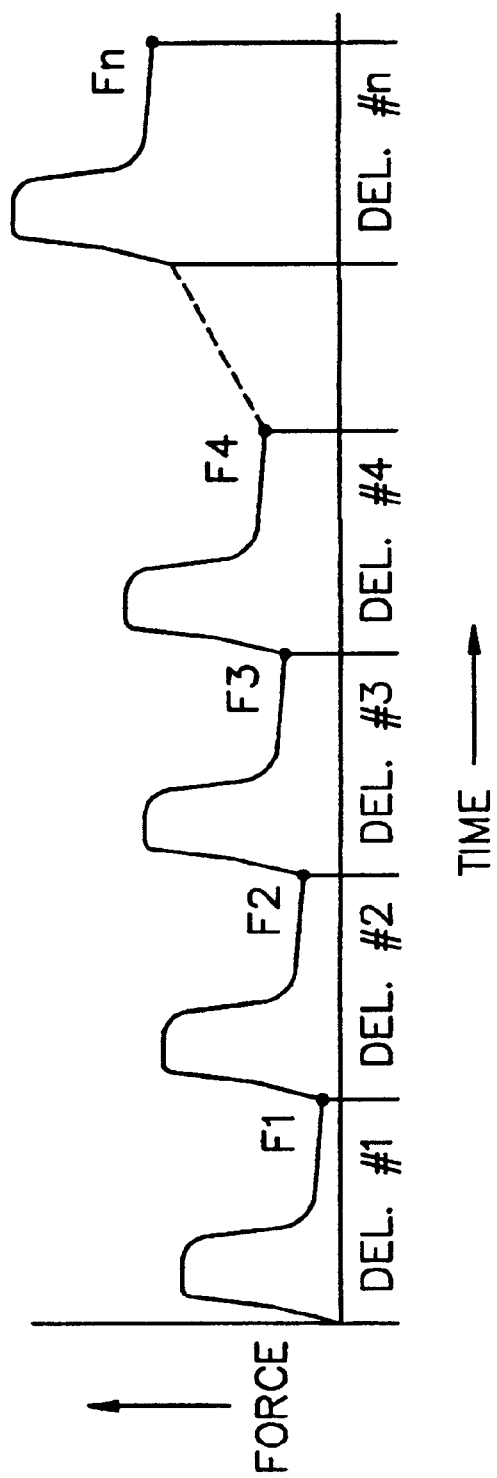
FIG. 14 is a graph of force v. time showing the sampling of force data prior to the initiation of a delivery cycle.
Figure 15:
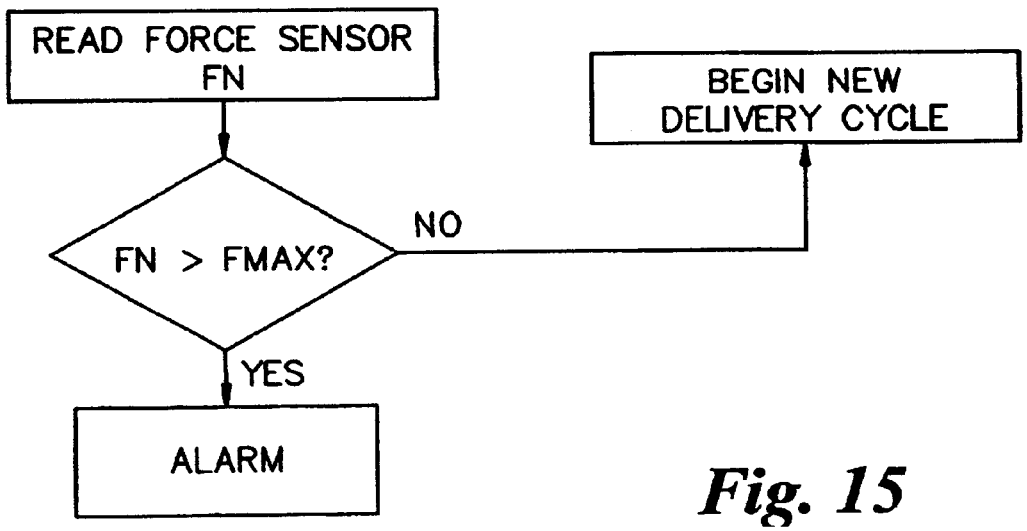
FIGS. 15–19 are flow charts showing individual system failure detection methods in accordance with the preferred method of FIG. 13.
Figure 16:
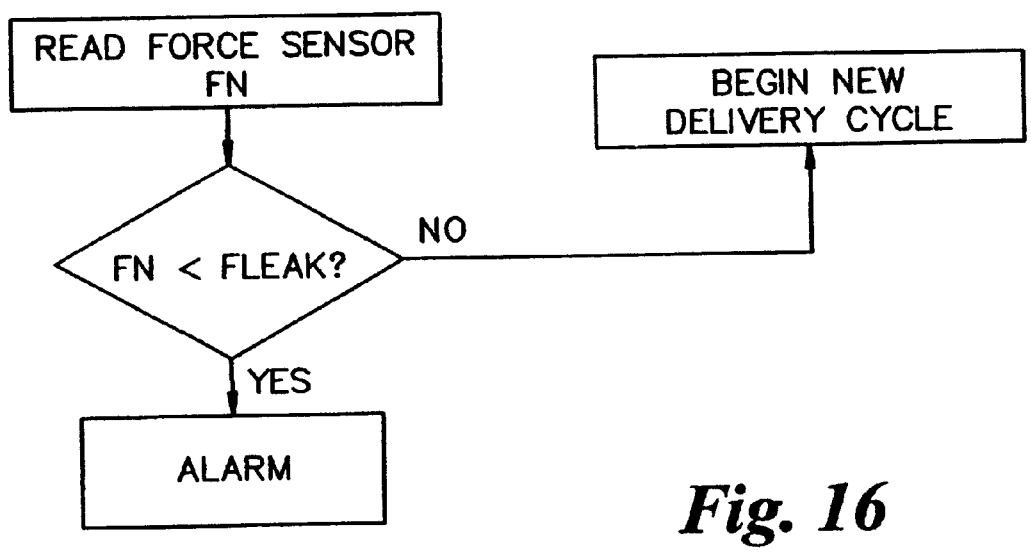
Figure 17:
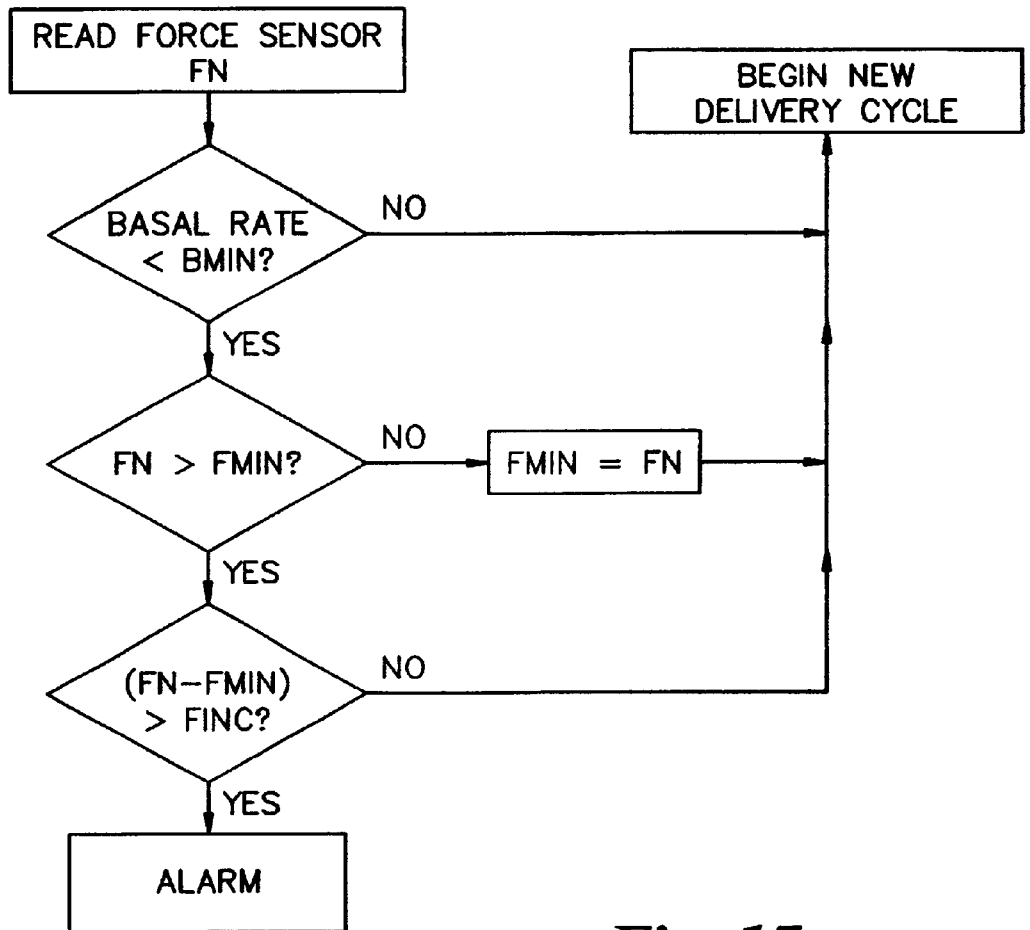

Referring now to FIG. 14, a graph of four sequential force signals during an occlusion condition are shown. The force v time relation of an occlusion is apparent from the figure, as the amount of force immediately preceding each delivery cycle is shown as higher than the preceding cycle, indicating the presence of an occlusion in the infusion path 14. FIG. 14 represents the condition which the method of FIG. 18 detects.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

We claim:

1. An occlusion detector for use with an infusion pump for dispensing volumetrically proportioned doses of pharmaceutical product to a patient, the infusion pump having a pharmaceutical storage area for containing a supply of pharmaceutical product and adapted to be connected to, an infusion path between the storage area and the patient, an incrementally operated urging mechanism for urging contents of the storage area to infuse a volumetrically proportioned dose of the contents along the infusion path to the patient, the urging mechanism traveling a complete increment in a delivery cycle, and a drive mechanism operably linked to the urging mechanism to control the incremental movement of the urging mechanism for dispensing a volumetrically proportioned dose of pharmaceutical product to the patient by way of the infusion path, the occlusion detector comprising:

a force transducer which provides a signal representative of force incident to the urging mechanism within the storage area;

a memory which stores information representative of the transducer signal;

a processor connected to the force transducer which monitors and receives the force transducer signal prior to a delivery cycle and actuation of the drive mechanism for dispensing of pharmaceutical product along the infusion path, the signal defined as a cycle signal, stores information representative of the cycle signal in the memory, compares a current cycle signal level to a previous cycle signal level stored in the memory and determines whether the current cycle signal level has increased over the previous cycle signal level to identify an increase in force incident to the urging mechanism within the storage area; and an alarm to alert the patient, triggered by the processor upon the identification of a predetermined number of increasing cycle signal levels whereby the increasing signal levels indicate an occlusion in the infusion path.

2. The occlusion detector of claim 1 wherein the processor monitors the force transducer immediately prior to actuation of the drive mechanism.

3. The occlusion detector of claim 2 wherein the processor compares a basal rate of the infusion to a predetermined basal rate prior to comparing the cycle signal levels.

4. The occlusion detector of claim 3 wherein cycle signal levels below the predetermined basal rate of infusion are compared to a predetermined signal value and cycle signal levels exceeding said predetermined signal value by a predetermined amount trigger the alarm.

5. A method of detecting an occlusion along an infusion path of an infusion pump having a pharmaceutical storage area for containing a supply of pharmaceutical product, and adapted to be connected to the infusion path between the storage area and a patient, an incrementally engaged urging mechanism for urging contents of the storage area to infuse a volumetrically proportioned dose of the contents along the infusion path to the patient, a force transducer for providing a signal representative of the force incident to the urging mechanism within the storage area, and a drive mechanism operably linked to the urging mechanism to control the incremental movement of the urging mechanism for dispensing a volumetrically proportioned dose of pharmaceutical product to the patient by way of the infusion path, the method comprising:

monitoring the signal of the force transducer prior to delivery cycles and the actuation of the drive mechanism for delivering a dose of pharmaceutical product to the patient, the signal defined as a cycle signal;

storing information representative of the cycle signals of the force transducer in a memory;

comparing a current cycle signal of the force transducer to a previous cycle signal stored in the memory for identifying an increase in force incident to the urging mechanism within the storage area;

determining whether the current cycle signal level has increased over the preceding cycle signal level;

counting each such increase; and activating an alarm when a predetermined number of force increases have been counted.

6. The method of claim 5 wherein the alarm is activated upon monitoring a predetermined number of sequential cycle increases.

7. The method of claim 5 further comprising the step of comparing the cycle signals to a predetermined value and activating the alarm if a cycle signal is greater than the predetermined value.

8. The method of claim 5 further comprising the step of comparing the cycle signals to a predetermined value and activating the alarm if a cycle signal is less than the predetermined value.

9. The method of claim 5 wherein the monitoring function is performed by a processor.

10. A method of detecting an occlusion along an infusion path of an infusion pump having a pharmaceutical storage area for containing a supply of pharmaceutical product adapted to be connected to the infusion path between the storage area and a patient, an incrementally operated urging mechanism for urging contents of the storage area to infuse a volumetrically proportioned dose of the contents along the infusion path to the patient, a force transducer for providing a signal representative of the force incident to the urging mechanism within the storage area, and a drive mechanism operably linked to the urging mechanism to control the incremental movement of the urging mechanism for dispensing a volumetrically proportioned dose of pharmaceutical product to the patient by way of the infusion path, the method comprising:

monitoring the signal of the force transducer prior to delivery cycles and the actuation of the drive mechanism for delivering a dose of pharmaceutical product to the patient, the signal defined as a cycle signal;

storing information representative of the force transducer cycle signal in a memory;

comparing a current cycle signal of the force transducer to a previous cycle signal stored in the memory for identifying an increase in force incident to the urging mechanism within the storage area;

determining whether the current cycle signal level has increased over the preceding cycle signal level by an amount greater than a predetermined value; and activating an alarm when the current cycle signal has increased over the preceding cycle signal by an amount greater than the predetermined value.

11. A method of detecting an occlusion along an infusion path of an infusion pump having a pharmaceutical storage area for containing a supply of pharmaceutical product adapted to be connected to the infusion path between the storage area and a patient, an incrementally engaged urging mechanism for urging contents of the storage area to infuse a volumetrically proportioned dose of the contents along the infusion path to the patient, a force transducer for providing a signal representative of the force incident to the urging mechanism within the storage area, and a drive mechanism operably linked to the urging mechanism to control the incremental movement of the urging mechanism for dispensing a volumetrically proportioned dose of pharmaceutical product to the patient by way of the infusion path, the method comprising:

monitoring the signal of the force transducer prior to delivery cycles and the actuation of the drive mechanism for delivering a dose of pharmaceutical product to the patient, the signal defined as a cycle signal;

determining whether the basal rate of the pharmaceutical delivery is less than a predetermined rate;

determining whether a current cycle signal for a basal rate less than the predetermined rate is less than a predetermined minimum value;

comparing the cycle signal of the force transducer to the predetermined minimum value;

determining whether the current cycle signal level has increased over the predetermined minimum value by more than a predetermined amount; and activating an alarm upon the determination of a force increase above the predetermined amount.

12. A system fault detector for use with an infusion pump for dispensing volumetrically proportioned doses of pharmaceutical product to a patient, the system fault detector comprising:

a force transducer which provides signals representative of a force incident to an urging mechanism within the infusion pump; and a processor which controls the urging mechanism and monitors the signals from the force transducer prior to a plurality of pump delivery cycles, wherein the processor stores information representative of the signals from the force transducer in a memory for the plurality of delivery cycles, receives a current force signal of a current delivery cycle from the force transducer immediately prior to actuating the drive mechanism during a delivery cycle, compares the current force signal to a previous force signal of a previous delivery cycle, determines whether the current force signal represents a force increase over the previous force signal, counts the number of sequential force increases between pump delivery cycles, and activates an alarm upon identification of a predetermined number of force increases.

13. The system fault detector of claim 12 wherein the processor further compares a current basal rate of infusion to a predetermined basal rate prior to comparing the current force signal to the previous force signal, and wherein the processor compares the current force signal to a predetermined minimal signal level if the basal rate of infusion is below the predetermined basal rate of infusion, and triggers an alarm if the current force signal exceeds the pregetermined minimal signal level by a predetermined amount.

14. The system fault detector of claim 12 wherein the processor further compares the current force signal to a predetermined maximum value and triggers the alarm if the current force signal is greater than the predetermined maximum value.

15. The system fault detector of claim 12 wherein the processor further compares the current force signal to a predetermined minimum value and triggers the alarm if the current force signal is less than the predetermined minimum value.

16. The system fault detector of claim 12 wherein the processor further compares the current force signal to the previous force signal and triggers the alarm if the current force signal is greater than the previous force signal by a predetermined value.

17. A method of detecting an occlusion along an infusion path and/or within a storage area of an infusion pump, the method comprising:

monitoring signals from a force transducer prior to a plurality of pump delivery cycles, to detect the force incident to an urging mechanism within the infusion pump;

storing information representative of the force signals in a memory for the plurality of delivery cycles;

comparing a force signal for a current delivery cycle to a force signal for a previous delivery cycle to determine whether the force signal for the current delivery cycle represents a force increase over the force signal for the previous delivery cycle;

counting the number of sequential increases in force between pump delivery cycles; and activating an alarm when a predetermined number of force increases have been counted.

18. A method of detecting an occlusion along an infusion path and/or within a storage area of an infusion pump, the method comprising:

monitoring signals from a force transducer prior to a plurality of pump delivery cycles, to detect the force incident to an urging mechanism within the infusion pump;

storing information representative of the force signals in a memory for the plurality of pump delivery cycles;

comparing a force signal for a current delivery cycle, defined as a current force signal, to a force signal for a previous delivery cycle, defined as a previous force signal, to determine whether the current force signal represents a force increase over the previous force signal by an amount greater than a predetermined value; and activating an alarm if the current force signal has increased over the previous force signal by an amount greater than the predetermined value.

19. A method of detecting an occlusion along an infusion path and/or within a storage area of an infusion pump, the method comprising:

monitoring signals from a force transducer prior to a plurality of pump delivery cycles, to detect the force incident to an urging mechanism within the infusion pump;

determining whether the basal rate of a current delivery cycle is less than a predetermined rate;

if the basal rate is less than the predetermined rate, determining whether a force signal for the current delivery cycle, defined as a current force signal, represents a force level less than a minimum force level;

if the current force signal is less then the minimum force level, storing the current force signal in a memory as the minimum force level;

if the current force signal is greater than the minimum force level, determining if the current force signal represents a force level higher than the minimum force level by an amount greater than a predetermined force increase value; and activating an alarm upon determination of a force increase greater than the predetermined force increase value.

20. A method of detecting an occlusion along an infusion path and/or within a storage area of an infusion pump, the method comprising:

monitoring signals from a force transducer prior to a plurality of pump delivery cycles, to detect the force incident to an urging mechanism within the infusion pump;

comparing a force signal for a current delivery cycle to a predetermined maximum value; and activating an alarm if the force signal for the current delivery cycle exceeds the predetermined maximum value.

21. A method of detecting leakage along an infusion path and/or within a storage area of an infusion pump, the method comprising:

monitoring signals from a force transducer prior to a plurality of pump delivery cycles, to detect the force incident to an urging mechanism within the infusion pump;

comparing a force signal for a current delivery cycle to a predetermined minimum value; and activating an alarm if the force signal for the current delivery cycle is less than the predetermined minimum value.

* * * * *

UNITED STATES PATENT AND TRADEMARK OFFICE
CERTIFICATE OF CORRECTION

PATENT NO. : 6,656,148 B2
DATED : December 2, 2003
INVENTOR(S) : Kusal K. Das et al.

It is certified that error appears in the above-identified patent and that said Letters Patent is hereby corrected as shown below:

Column 11,
Line 64, "to, an" should read -- to an --.

Column 14,
Lines 42-43, "pregetermined" should read -- predetermined --.

Column 16,
Line 3, "less then" should read -- less than --.

Signed and Sealed this

Third Day of February, 2004

JON W. DUDAS
*Acting Director of the United States Patent and Trademark Office*